(12) United States Patent
Nojiri et al.

(10) Patent No.: US 7,601,340 B2
(45) Date of Patent: Oct. 13, 2009

(54) HAIR COSMETIC COMPOSITION

(75) Inventors: Masayoshi Nojiri, Tokyo (JP); Minoru Nagai, Tokyo (JP)

(73) Assignee: Kao Corporation, Tokyo (JP)

( * ) Notice: Subject to any disclaimer, the term of this patent is extended or adjusted under 35 U.S.C. 154(b) by 886 days.

(21) Appl. No.: 11/082,769

(22) Filed: Mar. 18, 2005

(65) Prior Publication Data

US 2005/0220743 A1  Oct. 6, 2005

(30) Foreign Application Priority Data

Mar. 25, 2004 (JP) ............... 2004-088686

(51) Int. Cl.
 *A61Q 5/00* (2006.01)
 *A61Q 5/02* (2006.01)
 *A61Q 5/06* (2006.01)

(52) U.S. Cl. ............... 424/70.28; 424/70.11; 424/70.15

(58) Field of Classification Search ........................ None
 See application file for complete search history.

(56) References Cited

U.S. PATENT DOCUMENTS

| 4,530,829 | A | * | 7/1985 | Abe | .................. | 424/70.14 |
| 4,898,725 | A | | 2/1990 | Hoeffkes et al. | | |
| 5,403,517 | A | | 4/1995 | Horinishi et al. | | |
| 5,683,685 | A | * | 11/1997 | Hirano et al. | ............ | 424/78.03 |

FOREIGN PATENT DOCUMENTS

| EP | 1 174 112 A2 | 1/2002 |
| GB | 109523 | 12/1967 |
| JP | 58-046011 | 3/1983 |
| JP | 63-159310 | 7/1988 |
| JP | 01-093515 | 4/1989 |
| JP | 05-017322 | 1/1993 |
| JP | 6-298625 | 10/1994 |
| JP | 7-112921 | 5/1995 |
| JP | 9-301831 | 11/1997 |
| JP | 2000-109411 | 4/2000 |
| JP | 2002-047142 | 2/2002 |
| JP | 2003-055160 | 2/2003 |
| JP | 2004-035434 | 2/2004 |

OTHER PUBLICATIONS

JP 11-199445 (Jul. 27, 1999) Abstract.

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

Provided is a hair cosmetic composition, which contains the following components (A) and (B):
(A) a hydroxy-free tricarboxylic acid having from 4 to 20 carbon atoms in total, or salt thereof, and (B) at least one or more organic solvents selected from the group consisting of aromatic alcohols, N-alkylpyrrolidones, alkylene carbonates, polypropylene glycols, lactones and cyclic ketones, wherein the organic solvent has a ClogP of from −2 to 3; and wherein the hair cosmetic composition has a pH of from 2 to 5 at 25° C. when diluted to 20 times the weight with water. Provided also is a hair quality improving method which comprises treating the hair with the hair cosmetic composition.

The hair cosmetic composition of the present invention can for example give strength/body, manageability, and set retention property to the hair which is apt to be dry and moistureless owing to the damage by coloring, permanent waving, or repetition of excessive blow drying.

7 Claims, No Drawings

HAIR COSMETIC COMPOSITION

FIELD OF THE INVENTION

The present invention relates to a hair cosmetic composition containing a hydroxy-free tricarboxylic acid for providing benefits such as improving strength/body, manageability, setting power and feel of the hair.

BACKGROUND OF THE INVENTION

In recent years, it has been said that owing to the influence of chemical treatment such as hair coloring or physical treatment by blow drying, cuticles on the hair surface peel off or the hair becomes porous by the efflux of lipids from the inside of the hair and as a result, the hair inevitably becomes excessively dry, resistant to finger combing, difficult to style and manage, and lusterless.

Commercially available hair cosmetic compositions which have been popularly used for providing the hair with manageability and protecting the hair from excessive drying are, for example, emulsion type products such as hair cream having wax, higher alcohol and surfactant, and gels having a film forming polymer (set polymer). Such hair cosmetic compositions can temporarily overcome the problems such as poor manageability and excessive dryness by causing an oil or fat or a polymer to adhere to the hair surface, but cannot fundamentally improve the strength/body or manageability of the hair.

Some hair cosmetic compositions for improving the hair quality are known. Compositions using a specific organic acid and organic solvent which intend to improve the hair quality by acting on the inside of the hair are known (refer to, for example, JP-A-1995-112921, JP-A-1994-172131, JP-A-1997-301831 and JP-A-1994-298625). These compositions promote manageability of the hair by softening the hair which is stiff and therefore, hard to handle.

SUMMARY OF THE INVENTION

In the present invention, there is thus provided a hair cosmetic composition, which contains the following components (A) and (B):

(A) a hydroxy-free tricarboxylic acid having from 4 to 20 carbon atoms in total, or salt thereof, and (B) at least one or more organic solvents selected from the group consisting of aromatic alcohols, N-alkylpyrrolidones, alkylene carbonates, polypropylene glycols, lactones and cyclic ketones, wherein the organic solvent has a ClogP of from −2 to 3; and wherein the hair cosmetic composition has a pH of from 2 to 5 at 25° C. when diluted to 20 times the weight with water.

In another aspect of the invention, there is also provided a hair quality improving method, which comprises treating the hair with the above-described hair cosmetic composition.

DETAILED DESCRIPTION OF THE INVENTION

The present invention relates to a hair cosmetic composition capable of essentially improving the hair quality, improving luster and manageability of the hair, and providing excellent feel of the hair. In the present invention, the term "hair quality improvement" means improvement of strength/body, manageability, feel of the hair and set retention property of the hair.

The present inventors have found that by incorporating both a hydroxy-free tricarboxylic acid having a predetermined number of carbon atoms or salt thereof and a penetration-promoting organic solvent in a hair cosmetic composition, the penetration of the organic polycarboxylic acid and organic solvent is promoted and thus the strength/body, manageability, feel of the hair and set retention property under high humidity are improved.

Examples of the hydroxy-free tricarboxylic acid having from 4 to 20 carbon atoms in total, as Component (A) include 1,2,4-benzenetricarboxylic acid, 1,3,5-benzenetricarboxylic acid, 1,2,3-benzenetricarboxylic acid, 1,2,3-propanetricarboxylic acid, 2-methyl-1,2,3-propanetricarboxylic acid, 1,3,5-pentanetricarboxylic acid, 1,2,3-cyclopropanetricarboxylic acid, and cis-propene-1,2,3-tricarboxylic acid. Of these, tricarboxylic acids having from 4 to 12 are preferred, with those having from 6 to 9 carbon atoms are more preferred. Specific preferred examples include 1,2,4-benzenetricarboxylic acid, 1,3,5-benzenetricarboxylic acid, 1,2,3-benzenetricarboxylic acid, 1,2,3-propanetricarboxylic acid and 2-methyl-1,2,3-propanetricarboxylic acid. Among them, preferred is 1,2,3-propanetricarboxylic acid. Examples of the salt of these tricarboxylic acids include salts with an alkali metal, alkaline earth metal, ammonia or organic amine compound.

As Component (A), two or more of these compounds may be used in combination. The content of Component (A) in the hair cosmetic composition of the invention is preferably from 0.01 to 30 wt. %, more preferably from 0.1 to 20 wt. %, even more preferably from 0.5 to 10 wt. % in consideration of strength/body imparting effect, set retention improving effect and manageability improving effect.

The organic solvent to be used as Component (B) is selected from the group consisting of aromatic alcohols, N-alkylpyrrolidones, alkylene carbonates, polypropylene glycols, lactones and cyclic ketones. Specific examples include the following (b1) to (b5), respectively.

(b1) Aromatic alcohols represented by the formula (1):

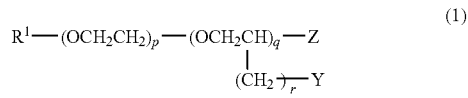

wherein, $R^1$ represents a group $R^2$—Ph—$R^3$— ($R^2$: a hydrogen atom, a methyl group or a methoxy group, $R^3$: a bond or a saturated or unsaturated divalent $C_{1-3}$ hydrocarbon group, Ph: paraphenylene group), Y and Z each represents a hydrogen atom or a hydroxy group, and p, q and r each stands for an integer of from 0 to 5, with the proviso that when p=q=0, Z does not represent a hydrogen atom and $R^1$ does not represent a group $R^2$—Ph—.

(b2) N-alkylpyrrolidones having a nitrogen atom to which a $C_{1-18}$ alkyl group has been bonded.

(b3) $C_{2-4}$ Alkylene carbonates.

(b4) Polypropylene glycols having a number average molecular weight of from 100 to 1000.

(b5) Lactones or cyclic ketones represented by any one of the formulas (2), (3) and (4):

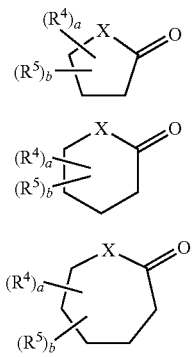

wherein, X represents a methylene group or an oxygen atom, $R^4$ and $R^5$ respectively represent substituents which are different from each other, and a and b each stands for 0 or 1.

Of the organic solvents serving as Component (B), examples of (b1) include benzyl alcohol, cinnamyl alcohol, phenethyl alcohol, p-anisyl alcohol, p-methylbenzyl alcohol, phenoxyethanol, and 2-benzyloxyethanol; those of (b2) include N-methylpyrrolidone, N-octylpyrrolidone and N-laurylpyrrolidone; and those of (b3) include ethylene carbonate and propylene carbonate. As the polypropylene glycol (4) having a number average molecular weight of from 100 to 1000, those having a number average molecular weight of from 200 to 600 are preferred. In (b5), $R^4$ and $R^5$ in the formulas (2) to (4) are each preferably a linear, branched or cyclic alkyl group, hydroxy group, sulfonic acid group, phosphoric acid group, carboxy group, phenyl group, sulfoalkyl group, phosphoric acid alkyl group and carboxyalkyl group. Of these, linear or branched $C_{1-6}$ alkyl groups—such as methyl, ethyl, propyl, isopropyl and butyl—substituted at the γ position in the case of γ-lactone and substituted at the δ position (methylene adjacent to the hetero oxygen atom) in the case of δ-lactone are preferred. In order to enhance the water solubility of the compounds (2) to (4), $R^4$ or $R^5$ preferably represents an acid group such as sulfonic acid group, phosphoric acid group or carboxy group, or an alkyl group substituted therewith. In (b5), examples of the lactone include γ-butyrolactone, γ-caprolactone, γ-valerolactone, δ-valerolactone, δ-caprolactone and δ-heptanolactone. Of these, γ-lactone is preferred, with γ-butyrolactone and γ-caprolactone being more preferred. Examples of the cyclic ketone as (b5) include cyclopentanone, cyclohexanone, cycloheptanone and 4-methylcycloheptanone.

Examples of the preferred Component (B) include benzyl alcohol, benzyloxyethanol, propylene carbonate, γ-butyrolactone and polypropylene glycol (number average molecular weight of from 300 to 500, preferably 400).

Component (B) to be used in the invention is preferably a liquid at 25° C. and has a ClogP of from −2 to 3, preferably from −1 to 2 in view of penetration promotion. The term "ClogP" as used herein means a measure indicating the distribution of a substance between an octanol phase and an aqueous phase. It is a calculated value of an octanol-water distribution coefficient (logP) as defined by the below-described equation and its examples are described in Chemical Reviews, 71(6), 1971.

$$\log P = \log([\text{Substance}]_{octanol}/[\text{Substance}]_{water})$$

wherein, $[\text{Substance}]_{octanol}$ means a mole concentration of a substance in a 1-octanol phase, while $[\text{Substance}]_{water}$ means a mole concentration of the substance in an aqueous phase.

The ClogP of each of the main compounds usable as Component (B) is as follows: benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and γ-butyrolactone (−0.64).

As Component (B), two or more compounds may be used in combination. Their content in the hair cosmetic composition of the invention is preferably from 0.1 to 40 wt. %, more preferably from 0.5 to 10 wt. %, even more preferably from 1 to 5 wt. % in view of its feeling upon use, and promotion of hair quality improving effects (improvement of elasticity, improvement of moisture resistance, and the like).

A weight ratio (A):(B) of the organic polycarboxylic acid or salt thereof as Component (A) to the organic solvent as Component (B) preferably ranges from 10:1 to 1:7, more preferably from 4:1 to 1:3 in order to effectively develop strength/body imparting effect, set retention improving effect and manageability improving effect of the hair.

The hair cosmetic composition of the invention may further contain ethanol. Ethanol contributes to the solubilization or stable dispersion of Component (B). The content of ethanol in the hair cosmetic composition of the invention is preferably from 0.01 to 50 wt. %, more preferably from 1 to 20 wt. %. A weight ratio of ethanol to Component (B) preferably ranges from 40:1 to 1:1, even more preferably from 20:1 to 3:1 from the viewpoint of penetration promotion of Components (A) and (B) into the hair.

In the hair cosmetic composition of the invention, a surfactant may be incorporated from the viewpoints of stability of the system including the solubilization or dispersion of the solvent, and improvement in the feel of the hair. As the surfactant, any one of cationic surfactant, nonionic surfactant, amphoteric surfactant and anionic surfactant can be used.

Examples of the cationic surfactant include quaternary ammonium salts represented by the following formula (5):

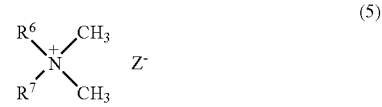

wherein $R^6$ and $R^7$ each independently represents a hydrogen atom, a $C_{1-28}$ alkyl group or a benzyl group, with the proviso that they do not simultaneously represent a hydrogen atom, a benzyl group or a $C_{1-3}$ lower alkyl group, and $Z^-$ represents an anion.

Either one of $R^6$ and $R^7$ preferably represents an alkyl group having from 16 to 24 carbon atoms, more preferably 22 carbon atoms, even more preferably a linear alkyl group, while the other one represents a lower $C_{1-3}$ alkyl group, preferably a methyl group. Examples of the anion $Z^-$ include halide ions such as chloride ions and bromide ions, and organic anions such as ethyl sulfate ions and methyl carbonate ions. Of these, halide ions are preferred, with chloride ions being more preferred.

As the cationic surfactant, mono(long chain alkyl) quaternary ammonium salts are preferred. Specific examples include cetyltrimethylammonium chloride, stearyltrimethylammonium chloride, arachyltrimethylammonium chloride and behenyltrimethylammonium chloride. Of these, stearyltrimethylammonium chloride and behenyltrimethylammonium chloride are preferred.

Examples of the nonionic surfactant include polyoxyalkylene alkyl ethers, polyoxyalkylene alkenyl ethers, higher fatty acid sucrose esters, polyglycerin fatty acid esters, higher fatty acid mono- or di-ethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkyl amidoamine oxides. Of these, polyoxyalkylene alkyl ethers and polyoxyethylene hydrogenated castor oils are preferred, with polyoxyethylene alkyl ethers being more preferred.

As the amphoteric surfactant, imidazoline, carbobetaine, amidobetaine, sulfobetaine, hydroxysulfobetaine, and amidosulfobetaine can be used.

Examples of the anionic surfactant include alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfone fatty acid salts, N-acylamino acid surfactants, mono- or di-phosphate surfactants and sulfosuccinates. Examples of the counterion to the anionic residue of the above-described surfactants include alkali metal ions such as sodium ion and potassium ion, alkaline earth metal ions such as calcium ion and magnesium ion, ammonium ions, and alkanolamines having 1 to 3 alkanol groups with 2 or 3 carbon atoms (such as monoethanolamine, diethanolamine, triethanolamine and triisopropanolamine). Examples of the counterion to the cationic residue include halide ions such as chloride ions, bromide ions and iodide ions, methosulfate ions and saccharinate ions.

Of these, cationic surfactants are preferred in view of feel of the hair.

These surfactants may be used either singly or in combination of two or more. The content of the surfactant(s) in the hair cosmetic composition of the invention is preferably from 0.01 to 10 wt. %, more preferably from 0.05 to 3 wt. % in view of stability of the system including solubilization of the solvent and emulsification of an oily substance.

In the hair cosmetic composition of the invention, a conditioning component selected from silicones and oily substances can be incorporated in order to improve conditioning effects further. Examples of the silicones include dimethylpolysiloxanes, polyether-modified silicones, amino-modified silicones, carboxy-modified silicones, methylphenylpolysiloxane, fatty acid-modified silicones, alcohol-modified silicones, aliphatic alcohol-modified silicones, epoxy-modified silicones, fluorine-modified silicones, cyclic silicones, and alkyl-modified silicones. Of these, dimethylpolysiloxanes, polyether-modified silicones and amino-modified silicones are preferred. Dimethylpolysiloxanes, polyether-modified silicones and amino-modified silicones can impart the hair with good lubricity, smoothness and moist feel, respectively. In the invention, various silicones can be used either singly or in combination of two or more, depending on the desired performance. As the dimethylpolysiloxane, those having a viscosity of from 5 mm$^2$/s to 10 million mm$^2$/s can be used depending on the desired feel of the hair, wherein those having a viscosity of 10 million mm$^2$/s are often supplied in the form of an emulsion. Of these, those having a viscosity falling within a range of from 5000 mm$^2$/s to 10 million mm$^2$/s are preferred, with those having a viscosity of from 50000 mm$^2$/s to 10 million mm$^2$/s being more preferred. The term "polyether-modified silicones" is a generic name of polyoxyethylene/methylpolysiloxane copolymers and poly(oxyethylene/oxypropylene)methylpolysiloxane copolymers and those having various HLBs are known. Examples of the commercially available products thereof include "Silicone KF351A", "Silicone KF353A", "Silicone KF6008", "Silicone KF6016", "Silicone KF6011", and "Silicone KF6012" (each, trade name; product of Shin-etsu Chemical), and "SH3771C", "SH3773C", and "SH3775C" (each, trade name; product of Dow Corning Toray Silicone). As the amino-modified silicones, amodimethicone oil or an emulsion thereof is preferred. Their commercially available products are amodimethicone emulsion "SM8704C" (trade name; product of Dow Corning Toray Silicone) and "KT-1989" and "XF-42-B1989" (each, trade name; product of GE Toshiba Silicones).

The silicones may be used either singly or in combination of two or more. The content of the silicones in the hair cosmetic composition of the invention is preferably from 0.05 to 20 wt. %, more preferably from 0.1 to 10 wt. %, even more preferably from 0.5 to 5 wt. % in consideration of smoothness to facilitate finger combing and stickiness-free feel.

The oily substance is added to improve the hair manageability after drying. Examples thereof include hydrocarbons such as squalene, squalane, liquid isoparaffin, light liquid isoparaffin, heavy liquid isoparaffin, α-olefin oligomer, liquid paraffin and cycloparaffin; glycerides such as castor oil, cacao oil, mink oil, avocado oil and olive oil; waxes such as bees wax, sperm wax, lanolin, microcrystalline wax, ceresin wax and carnauba wax; higher alcohols such as cetyl alcohol, oleyl alcohol, stearyl alcohol, isostearyl alcohol and 2-octyldodecanol; esters such as octyldodecyl myristate, hexyl laurate, cetyl lactate, propylene glycol monostearate, oleyl oleate, hexadecyl 2-ethylhexanoate, isononyl isononanoate and tridecyl isononanoate; higher fatty acids such as capric cid, lauric acid, myristic acid, palmitic acid, stearic acid, behenic acid, oleic acid, coconut oil fatty acid, isostearic acid and isopalmitic acid; and other oils such as isostearyl glyceryl ether and polyoxypropylene butyl ether. Of these, branched hydrocarbons including squalene, squalane, liquid isoparaffin, light liquid isoparaffin, heavy liquid isoparaffin, α-olefin oligomer are preferred.

These oily substances may be used either singly or in combination of two or more. The content of the oily substance in the hair cosmetic composition of the invention is preferably from 0.05 to 20 wt. %, more preferably from 0.1 to 10 wt. %, even more preferably from 0.5 to 5 wt. % in view of good manageability and stickiness-free feel.

The hair cosmetic composition of the invention may further contain a water soluble polymer in view of improvement of hair styling property, regulation of viscosity, stability, improvement of adhesion upon application to the hair, improvement of feel of the hair and early expression of hair quality improving effect. The water soluble polymer preferably has a weight average molecular weight of from 10000 to 5000000, more preferably from 100000 to 1000000. Examples of such a polymer include polyvinylpyrrolidone polymer compounds such as polyvinylpyrrolidone, vinylpyrrolidone/vinyl acetate copolymer, vinylpyrrolidone/vinyl acetate/vinyl propionate tertiary copolymer, vinylpyrrolidone/alkylaminoacrylate (quaternary chloride) copolymer, vinylpyrrolidone/acrylate/(meth)acrylic acid copolymer, and vinylpyrrolidone/alkylaminoacrylate/vinylcaprolactam copolymer; acidic vinyl ether polymer compounds such as methyl vinyl ether/maleic anhydride alkyl half ester copolymer; acidic polyvinyl acetate polymer compounds such as vinyl acetate/crotonic acid copolymer, vinyl acetate/crotonic acid/vinyl neodecanoate copolymer and vinyl acetate/crotonic acid/vinyl propionate copolymer, acidic acrylic polymer compounds such as (meth)acrylic acid/(meth)acrylate copolymer, and acrylic acid/alkyl acrylate/alkylacrylamide copolymer; amphoteric acrylic polymer compounds such as N-methacryloylethyl-N,N-dimethylammonium-α-N-methylcarboxybetaine/butyl methacrylate copolymer, and hydroxypropyl acrylate/butylaminoethyl methacrylate/acrylic octylamide copolymer; basic acrylic polymer compounds such as acrylamide/acrylate quaternary copolymer; cationic celluloses; and hydroxyethyl cellulose, methyl cellulose, cationic guar gums, diallyl quaternary ammonium salt/acrylamide copolymers, and chitin/chitosan derivatives such as hydroxypropyl chitosan, carboxymethyl chitin, and carboxymethyl chitosan.

These water soluble polymers may be used either singly or in combination of two or more. Their content in the hair cosmetic composition of the invention is preferably from 0.1 to 10 wt. %, more preferably from 0.5 to 5 wt. %.

The hair cosmetic composition of the invention may further contain a polyhydric alcohol. The polyhydric alcohol contributes to solubilization and stable dispersion of Component (B). In addition, the improvement of luster and enhancement of the hair quality improving effect are accelerated by the synergistic action between the polyhydric alcohol and Component (B). Examples of the polyhydric alcohol include ethylene glycol, glycerin, sorbitol, propylene glycol, 1,3-butyleneglycol and dipropylene glycol. Of these, glycerin is preferred. These polyhydric alcohols may be used either singly or in combination of two or more. Their content in the hair cosmetic composition of the invention is preferably from 0.1 to 10 wt. %, more preferably from 0.5 to 5 wt. %.

The hair cosmetic composition of the invention may further contain, as needed, components employed for ordinary hair cosmetic compositions depending on their purpose of use. Examples of such components include antidandruffs, vitamin preparations, bactericides, anti-inflammatories, antiseptics, chelating agents, humectants such as panthenol, coloring agents such as dyes and pigments, viscosity regulators such as polyethylene glycol and clay mineral, plant extracts, pearling agents, perfumes, colorants, ultraviolet absorbers, antioxidants, and the other components as described in the ENCYCLOPEDIA OF SHAMPOO INGREDIENTS (MICELLE PRESS).

The hair cosmetic composition of the invention is adjusted to have a pH of from 2 to 5 (at 25° C. when diluted to 20 times the weight with water), preferably from 2.5 to 4, more preferably from 3 to 4 in order to develop the performances of the composition fully, for example, to improve the strength/body of the hair and to give manageability to the hair. It is preferred to use sodium hydroxide or potassium hydroxide in order to regulate the pH to fall within the above-described range when Component (A) is added in an amount necessary for bringing about strength/body improving effect.

Moreover, to accelerate the penetration of the organic acid and organic solvent to the hair, cause the hair quality improving effects to appear promptly and improve the feeling?, the hair cosmetic composition of the invention may contain an organic acid or inorganic acid, or salt thereof other than Component (A). Examples of the organic acid include, in addition to Component (A), malonic acid, succinic acid, glutaric acid, adipic acid, maleic acid, fumaric acid, phthalic acid, oxalic acid, malic acid, tartaric acid, lactic acid, glycolic acid, citric acid, revulinic acid, butyric acid, valeric acid and mandelic acid; those of the inorganic acid include phosphoric acid, sulfuric acid and nitric acid; and those of the salt of these acids include alkali metal salts such as sodium salt and potassium salt, ammonium salts, and alkanolamine salts such as triethanolamine salt.

The form of the hair cosmetic composition of the invention may be selected from liquid, gel, paste, cream and wax as needed, but the composition in the form of a solution using, as a solvent, water or a lower alcohol are preferred, with water being more preferred.

The hair cosmetic composition of the invention is preferably used as a hair shampoo, hair styling agent or hair conditioning agent. It can be provided, for example, as a pump spray, aerosol spray, pump foam, aerosol foam, gel, lotion, cream or wax.

By heating after application of the hair cosmetic composition of the invention to the hair, penetration of Components (A) and (B) into the hair can be accelerated. For heating, a drier, heater, hair curling iron or hair iron can be used. The heating temperature is preferably 60° C. or greater, more preferably 70° C. or greater.

EXAMPLES

The present invention will hereinafter be described in further detail by examples. It should however be borne in mind that the present invention is not limited to or by them.

The pH in the below-described examples and comparative examples are those at 25° C. when diluted to 20 times the weight with water.

Example 1

Hair cosmetic compositions as shown in Table 1 were prepared and their "setting property", "set retention property", "manageability", and "strength/body improving effect" were evaluated. The results are shown in Table 2.

(Evaluation Method)

Evaluation of "setting property" and "set retention property"

1) Hair Bundle to be Evaluated

A hair bundle of 10 cm in length, 1.5 cm in width and 1 g in weight was made using the hair of a Japanese female whose hair was not subjected to chemical treatment such as permanent waving or hair coloring. The hair bundle was bleached (by "Ravenus Color Appeal Inazuma Bleach"; product of Kao) twice and the resulting hair bundle was provided for the evaluation of its setting property.

2) Treatment of the Hair Bundle

After the hair bundle to be evaluated was shampooed (with "Ravenus Designing Shampoo", product of Kao) and towel dried, it was dipped in 10 g of the example product or comparative product (which will hereinafter be called "treating agent") at 40° C. for 180 minutes, and then dried for 10 minutes with hot air of 70° C. Then, 0.1 g of water was applied to the hair bundle. The resulting hair bundle was wound around a rod having a diameter of 4 cm and dried for 30 minutes in a drier of 75° C.

3) Procedures and Criteria of Evaluation

The bundle thus set was allowed to stand for 1 hour at 20° C. in 65% RH. It was then removed from the rod and suspended from a stage and a setting ratio just after treatment was evaluated. It was then suspended in a thermo-hygrostat (25° C. and 96% RH) to determine the set retention power. The set retention power was determined in the following manner. The length of the hair bundle thus suspended (distance from the bundled position to the end of the hair) was measured. Supposing that the initial length (10 cm) of the hair bundle before curling was a length at a set retention ratio of 0%, a relative length of the hair bundle just after suspension (setting ratio just after suspension; %) and a relative length of the hair bundle after suspension in the thermo-hygrostat for 40 minutes (setting ratio after 40 minutes; %) were determined in accordance with the following equations, respectively:

Setting ratio just after suspension (%) =

$$\frac{\text{(initial length of the hair bundle)} - \text{(length of the hair bundle just after suspension)}}{\text{(initial length of the hair bundle)}} \times 100$$

Setting ratio after 40 minutes (%) =

$$\frac{\text{(initial length of the hair bundle)} - \text{(length of the hair bundle after 40 minutes)}}{\text{(initial length of the hair bundle)}} \times 100$$

Evaluation of "Manageability" and "Strength/Body Improving Effect"

The hair used in the above-described evaluation was allowed to stand for 24 hours at 20° C. in 65% RH. The manageability of the hair was observed visually, followed by evaluation of strength/body improving effect.

Evaluation Criteria

Organoleptic evaluation by a panel of 5 experts was performed in accordance with the below-described criteria and an average of the scores was determined.

(Manageability)

5: Excellent manageability

4: Some manageability

3: Cannot be said either way

2: A little inferior in manageability

1: Lack of manageability (Strength/Body Improving Effect)

5: Obvious improvement in strength/body

4: Improvement in strength/body

3: Slight improvement in strength/body

2: No improvement in strength/body

1: Deterioration in strength/body

TABLE 1

|  |  | Example product | | Comparative Product | | |
|---|---|---|---|---|---|---|
|  |  | 1 | 2 | 1 | 2 | 3 |
| Components mixed (wt. %) | 1,2,3-Propanetricarboxylic acid | 4.0 | 4.0 | — | — | — |
|  | Malic acid | — | — | 4.0 | — | — |
|  | Lactic acid | — | — | — | 4.0 | — |
|  | 2-Benzyloxyethanol | 10.0 | 10.0 | 10.0 | 10.0 | — |
|  | Ethanol | 15.0 | 15.0 | 15.0 | 15.0 | — |
|  | Water | Balance | Balance | Balance | Balance | 100.0 |
|  | Vinylpyrrolidone/N,N-dimethylaminoethyl methacrylic acid copolymer diethyl sulfate solution (20 wt. %) | — | 2.5 | — | — | — |
|  | Stearyltrimethylammonium chloride | — | 0.9 | — | — | — |
|  | Polyoxyethylene/methylpoly siloxane copolymer | — | 0.6 | — | — | — |
|  | Sodium hydroxide (pH regulator) | q.s. | q.s. | q.s. | q.s. | — |
| Evaluation | pH (25° C.) | 3.0 | 3.0 | 3.0 | 3.0 | 6.7 |
|  | Setting ratio just after suspension (%) | 74 | 78 | 62 | 38 | 32 |
|  | Setting ratio after 40 minutes (%) | 44 | 46 | 34 | 28 | 24 |
|  | Manageability | 4.2 | 4.4 | 3.8 | 2.8 | 1.6 |
|  | Strength · body improving effect | 3.8 | 4.0 | 3.6 | 2.2 | 1.2 |

It has been confirmed from the above-described results that good setting property, strength/body improving effect, and manageability improving effect can be attained according to the invention. It has also been confirmed that even after the removal of the components applied to the surface of the hair by shampooing, the above-described effects last, suggesting that the invention products are effective for improving the hair quality.

| | (wt. %) |
|---|---|
| Example 2: (Pump spray) | |
| 1,2,3-Propanetricarboxylic acid | 4.0 |
| Stearyltrimethylammonium chloride | 0.25 |
| Glycerin | 1.0 |
| 2-Benzyloxyethanol | 2.5 |
| Ethanol | 4.5 |
| Perfume | 0.02 |
| Water | Balance |
| Citric acid | 1.1 |
| Sodium hydroxide (pH regulator) | Amount to adjust pH to 3.7 |
| Example 3: (Pump mist) | |
| 1,2,3-Propanetricarboxylic acid | 3.5 |
| Malic acid | 1.0 |
| Propylene carbonate | 2.5 |
| Polyvinylpyrrolidone | 3.0 |
| Ethanol | 10.0 |
| Perfume | 0.05 |
| Water | Balance |
| Sodium hydroxide (pH regulator) | Amount to adjust pH to 3.7 |
| Example 4: (Hair gel) | |
| Stearyltrimethylammonium chloride | 0.25 |

-continued

| | (wt. %) |
|---|---|
| 1,2,3-Propanetricarboxylic acid | 2.5 |
| Succinic acid | 1.5 |
| Glycerin | 2.0 |
| 2-Benzyloxyethanol | 2.5 |
| Hydroxyethyl cellulose | 2.0 |

-continued

| | (wt. %) |
|---|---|
| Ethanol | 10.0 |
| Perfume | 0.05 |
| Water | Balance |
| Potassium hydroxide (pH regulator) | Amount to adjust pH to 3.7 |

Example 5: (Hair lotion)

| | |
|---|---|
| 1,2,4-Benzenetricarboxylic acid | 4.0 |
| 1,2,3-Propanetricarboxylic acid | 1.0 |
| Methylpolysiloxane (100 cs) | 1.0 |
| Glycerin | 1.0 |
| 2-Benzyloxyethanol | 2.5 |
| N-methylpyrrolidone | 1.0 |
| (Meta) acrylic acid/(meta) acrylate copolymer | 2.0 |
| Ethanol | 10.0 |
| Perfume | 0.02 |
| Water | Balance |
| Sodium hydroxide (pH regulator) | Amount to adjust pH to 3.7 |

Example 6: (Hair lotion)

| | |
|---|---|
| 1,3,5-Pentanetricarboxylic acid | 2.5 |
| 1,2,4-Benzenetricarboxylic acid | 1.5 |
| Tartaric acid | 1.0 |
| Stearyltrimethylammonium chloride | 0.1 |
| Benzyl alcohol | 2.0 |
| Polyethylene glycol 400 | 0.45 |
| Ethanol | 4.5 |
| Water | Balance |
| Potassium hydroxide (pH regulator) | Amount to adjust pH to 3.7 |

Example 7: (Pump foam)

| | |
|---|---|
| 1,2,4-Benzenetricarboxylic acid | 2.5 |
| 2-Methyl-1,2,3-propanetricarboxylic acid | 2.5 |
| Polyoxyethylene lauryl ether (16E.O.) | 1.0 |
| Stearyltrimethylammonium chloride | 0.1 |
| Glycerin | 1.0 |
| γ-Butyrolactone | 2.0 |
| Ethanol | 4.0 |
| Perfume | 0.02 |
| Water | Balance |
| Sodium hydroxide (pH regulator) | Amount to adjust pH to 3.7 |

Example 8: (Shampoo)

| | |
|---|---|
| 1,3,5-Pentanetricarboxylic acid | 1.0 |
| Sodium polyoxyethylene lauryl ether sulfate | 10.0 |
| Sodium lauryl sulfate | 4.0 |
| Lauramidopropyl betaine | 3.0 |
| Polyoxyethylene lauryl ether (16E.O.) | 2.0 |
| Coconut oil fatty acid monoethanolamide | 0.8 |
| Myristyl alcohol | 1.0 |
| Highly polymerized methyl polysiloxane (polymerization degree: 1000 to 3000) | 4.0 |
| Pearl concentrate | 8.0 |
| Polypropylene glycol (number average molecular weight: 400) | 1.0 |
| 2-Benzyloxyethanol | 0.5 |
| Cationic cellulose | 0.4 |
| Cationic guar gum | 0.2 |
| Sodium chloride | 0.25 |
| Sodium hydroxide (pH regulator) | Amount to adjust pH to 3.7 |
| Perfume | 0.5 |
| Water | Balance |

Example 9 (Conditioner)

| | |
|---|---|
| 1,2,4-Benzenetricarboxylic acid | 1.0 |
| Stearylamidopropyldimethylamine lactate | 3.5 |
| Stearyl alcohol | 6.0 |
| Dipentaerythritol fatty acid ester | 0.1 |
| Isopropyl palmitate | 0.5 |
| Methylpolysiloxane (polymerization degree: 1000 to 3000) | 2.5 |
| Isoparaffin | 2.5 |
| Phenoxyethanol | 0.1 |

-continued

| | (wt. %) |
|---|---|
| Polypropylene glycol (number average molecular weight: 400) | 2.0 |
| 2-Benzyloxyethanol | 1.0 |
| Glycolic acid | 1.0 |
| Sodium hydroxide (pH regulator) | Amount to adjust pH to 3.2 |
| Perfume | 0.4 |
| Water | Balance |

The invention claimed is:

1. A hair cosmetic composition comprising components (A) and (B):
   (A) 1,2,3-propanetricarboxylic acid or a salt thereof, and
   (B) 2-benzyloxyethanol; wherein component (A) is present in an amount from 0.5 to 10 wt % and component (B) is present in an amount from 0.5 to 10 wt % and wherein the hair cosmetic composition has a pH of from 2 to 5 at 25° C. when diluted 20 times by weight with water.

2. The hair cosmetic composition of claim 1, further comprising ethanol in an amount of 1 to 20 wt %.

3. The hair cosmetic composition of claim 1, further comprising at least one polyhydric alcohol, in an amount of 0.1 to 10 wt %, selected from the group consisting of ethylene glycol, glycerin, sorbitol, propylene glycol, 1,3-butyleneglycol and dipropylene glycol.

4. The hair cosmetic composition of claim 1, further comprising a surfactant wherein the surfactant is at least one cationic surfactant selected from the group consisting of quaternary ammonium salts represented by formula (5):

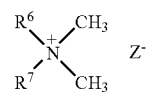

(5)

wherein $R^6$ and $R^7$ each independently represents a hydrogen atom, a $C_{1-28}$ alkyl group or a benzyl group, with the proviso that they do not simultaneously represent a hydrogen atom, a benzyl group or a $C_{1-3}$ lower alkyl group, and $Z^-$ represents an anion.

5. The hair cosmetic composition of claim 1, further comprising a water soluble polymer wherein the water soluble polymer is at least one selected from the group consisting of polyvinylpyrrolidone, vinylpyrrolidone/vinyl acetate copolymer, vinylpyrrolidone/vinyl acetate/vinyl propionate tertiary copolymer, vinylpyrrolidone/alkylaminoacrylate (quaternary chloride) copolymer, vinylpyrrolidone/acrylate/ (meth)acrylic acid copolymer, vinylpyrrolidone/alkylaminoacrylate/vinylcaprolactam copolymer, methyl vinyl ether/ maleic anhydride alkyl half ester copolymer, vinyl acetate/ crotonic acid copolymer, vinyl acetate/crotonic acid/vinyl neodecanoate copolymer, vinyl acetate/crotonic acid/vinyl propionate copolymer, (meth)acrylic acid/(meth)acrylate copolymer, acrylic acid/alkyl acrylate/alkylacrylamide copolymer, N-methacryloylethyl-N,N-dimethylammonium-α-N-methylcarboxybetaine/butyl methacrylate copolymer, hydroxypropyl acrylate/butylaminoethyl methacrylate/ acrylic octyl amide copolymer, acrylamide/acrylate quaternary copolymer, a cationic cellulose, hydroxyethyl cellulose, methyl cellulose, a cationic guar gum, a diallyl quaternary ammonium salt/acrylamide copolymer, hydroxypropyl chitosan, carboxymethyl chitin, and carboxymethyl chitosan.

6. The hair cosmetic composition of claim 5, wherein the water soluble polymer is present in an amount of 0.1 to 10 wt %.

7. A method for treating hair comprising applying to the hair the hair cosmetic composition of claim 1.

* * * * *

UNITED STATES PATENT AND TRADEMARK OFFICE
CERTIFICATE OF CORRECTION

PATENT NO. : 7,601,340 B2  Page 1 of 1
APPLICATION NO. : 11/082769
DATED : October 13, 2009
INVENTOR(S) : Nojiri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1244 days.

Signed and Sealed this

Fifth Day of October, 2010

David J. Kappos
*Director of the United States Patent and Trademark Office*